(12) United States Patent
Yaeger

(10) Patent No.: US 11,752,276 B2
(45) Date of Patent: Sep. 12, 2023

(54) SYRINGE CAPPING AND UNCAPPING DEVICE

(71) Applicant: David E. Yaeger, Telford, PA (US)

(72) Inventor: David E. Yaeger, Telford, PA (US)

( * ) Notice: Subject to any disclaimer, the term of this patent is extended or adjusted under 35 U.S.C. 154(b) by 171 days.

(21) Appl. No.: 17/346,690

(22) Filed: Jun. 14, 2021

(65) Prior Publication Data

US 2022/0395646 A1    Dec. 15, 2022

(51) Int. Cl.
*A61M 5/32*    (2006.01)

(52) U.S. Cl.
CPC ....... *A61M 5/3204* (2013.01); *A61M 2205/02* (2013.01)

(58) Field of Classification Search
CPC .............. A61M 5/3204; A61M 5/3205; A61M 5/3213; A61M 2005/3215
See application file for complete search history.

(56) References Cited

U.S. PATENT DOCUMENTS

| | | |
|---|---|---|
| 4,737,149 A | 4/1988 | Gillilan |
| 4,742,910 A | 5/1988 | Staebler |
| 4,767,412 A | 8/1988 | Hymanson |
| 4,781,697 A | 11/1988 | Slaughter |
| 4,846,803 A | 7/1989 | Emerson |
| 4,900,309 A | 2/1990 | Netherton et al. |
| 4,915,698 A | 4/1990 | Levenson |
| 4,981,476 A | 1/1991 | Aichlmayr et al. |
| 4,986,816 A * | 1/1991 | Steiner ................ A61M 5/3213 604/263 |
| 4,986,817 A | 1/1991 | Code |
| 5,067,944 A | 11/1991 | Nichols |
| 5,078,692 A | 1/1992 | Cuprak |
| 5,078,695 A | 1/1992 | Farrar, Jr. et al. |
| 5,183,469 A | 2/1993 | Capaccio |
| D335,182 S | 4/1993 | Drummond, Jr. |

(Continued)

FOREIGN PATENT DOCUMENTS

FR    2617719 A1    11/1990
GB    2209470 A    5/1989

(Continued)

OTHER PUBLICATIONS

Sharn Inc. Anesthesia, Guard-It Sterile Syringe Capping Card, https://www.sharn.com/safety-or/p/Guard-It-Sterile-Syringe-Capping-Card/, retrieved Jun. 11, 2011, pp. 1-2.

(Continued)

*Primary Examiner* — Dung T Ulsh
(74) *Attorney, Agent, or Firm* — The Belles Group, P.C.

(57) ABSTRACT

A syringe capping and uncapping device which includes a body portion and a flange portion. The body portion has a receptacle and a guard wall. The receptacle has an outer surface and an inner surface that defines a cavity configured to receive and hold a cap of a syringe. The guard wall circumferentially surrounds the outer surface of the receptacle. The flange portion extends radially outward from a top end of the body portion. A portion of the guard wall may be pivotably coupled to the flange portion so that a force applied onto the portion of the guard wall in an inward direction may cause the guard wall to pivot inwardly and compress the receptacle into forcible contact with the cap of the syringe held in the cavity to facilitate removal of the cap from the syringe.

20 Claims, 15 Drawing Sheets

(56) References Cited

U.S. PATENT DOCUMENTS

| | | | |
|---|---|---|---|
| 5,308,582 | A | 5/1994 | Serra |
| 5,554,126 | A | 9/1996 | Filley |
| 5,607,403 | A | 3/1997 | Kretzschmar et al. |
| D425,197 | S | 5/2000 | Comer et al. |
| 6,648,857 | B1 | 11/2003 | Pedigo |
| 6,719,737 | B2 | 4/2004 | Kobayashi |
| 8,603,039 | B2 | 12/2013 | Brand |
| 2005/0171484 | A1 | 8/2005 | Jangula |
| 2006/0258991 | A1 | 11/2006 | Lin |
| 2007/0191769 | A1 | 8/2007 | Meittunen |
| 2008/0210890 | A1 | 9/2008 | Fago |
| 2009/0014462 | A1* | 1/2009 | Costa ................ A61M 5/3205 221/185 |
| 2013/0012886 | A1 | 1/2013 | Kawachi et al. |
| 2013/0144219 | A1* | 6/2013 | Evans ................ A61M 5/3202 604/263 |
| 2020/0254190 | A1 | 8/2020 | Aneas |
| 2021/0030972 | A1* | 2/2021 | Valentin ............. A61M 5/3204 |

FOREIGN PATENT DOCUMENTS

| | | | |
|---|---|---|---|
| WO | 2003051423 | A2 | 6/2003 |
| WO | 2020070260 | A1 | 4/2020 |

OTHER PUBLICATIONS

International Search Report and the Written Opinion of PCT/US2022/29487 dated Sep. 22, 2022.

* cited by examiner

SYRINGE CAPPING AND UNCAPPING DEVICE

BACKGROUND OF THE INVENTION

Medical care often entails the use of syringes for introducing medication into the body of a patient or for withdrawing fluids from the patient for analysis. Furthermore, there are many laboratory settings in which people are tasked with using syringes to perform various tasks such as testing on animals, drug analysis, and the like. People who work with syringe needles understand that there is a risk of unintentionally pricking oneself with the needle by misalignment of the syringe needle when separating the syringe needle from or returning the syringe needle to a protective sheath. This can cause injury to the user and presents a risk of transmission of infectious disease. Thus, a need exists for a device to assist a user in attaching a protective sheath to a syringe needle and detaching the protective sheath from the syringe needle while protecting the user against unintentional needle pricks.

SUMMARY OF THE INVENTION

The invention is directed to a syringe capping and uncapping device which includes a body portion and a flange portion. The body portion has a receptacle and a guard wall. The receptacle has an outer surface and an inner surface that defines a cavity configured to receive and hold a cap of a syringe. The guard wall circumferentially surrounds the outer surface of the receptacle. The flange portion extends radially outward from a top end of the body portion. A portion of the guard wall may be pivotably coupled to the flange portion so that a force applied onto the portion of the guard wall in an inward direction may cause the guard wall to pivot inwardly and compress the receptacle into forcible contact with the cap of the syringe held in the cavity to facilitate removal of the cap from the syringe.

In one embodiment, the invention can be a syringe capping and uncapping device comprising: a body portion extending from a bottom end to a top end along a longitudinal axis, the body portion defining a cavity configured to receive and hold a cap of a syringe; an annular flange extending radially from the top end of the body portion, the annular flange surrounding an opening that provides a passageway into the cavity of the body portion; wherein the body portion comprises a first portion formed from a resilient material and a second portion formed from a rigid material, the second portion circumferentially surrounding the first portion; and wherein at least a portion of the body portion is configured to be compressed inwardly towards the longitudinal axis to apply pressure onto the cap of the syringe that is positioned in the cavity while the syringe is pulled axially to remove the cap from the syringe.

In another embodiment, the invention can be a syringe capping and uncapping device comprising: a body portion extending along a longitudinal axis, the body portion comprising: a receptacle comprising an outer surface and an inner surface defining a cavity configured to receive and hold a cap of a syringe; and a guard wall circumferentially surrounding the outer surface of the receptacle; a flange portion extending radially outward from a top end of the body portion; and wherein at least a portion of the guard wall is pivotably coupled to the flange portion so that a force applied onto the portion of the guard wall in an inward direction towards the longitudinal axis causes the portion of the guard wall to pivot inwardly and compress the receptacle into forcible contact with the cap of the syringe to facilitate removal of the cap from the syringe.

In yet another embodiment, the invention can be a syringe capping and uncapping device comprising: a body portion extending along a longitudinal axis, the body portion comprising: a receptacle comprising an outer surface and an inner surface defining a cavity configured to receive and hold a cap of a syringe; and a guard wall comprising a plurality of wall segments that collectively surround the receptacle, the plurality of distinct wall segments comprising a pair of pivotable wall segments; a flange portion extending from a top end of the body portion, the pair of pivotable wall segments coupled to the flange portion by a living hinge; and wherein the pair of pivotable wall segments are pivotably coupled to the flange portion so that a force applied onto the pair of pivotable wall segments in an inward direction towards one another causes pair of pivotable wall segments to pivot inwardly and compress the receptacle into forcible contact with the cap of the syringe to facilitate removal of the cap from the syringe.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein.

DETAILED DESCRIPTION OF THE INVENTION

Figure 1:
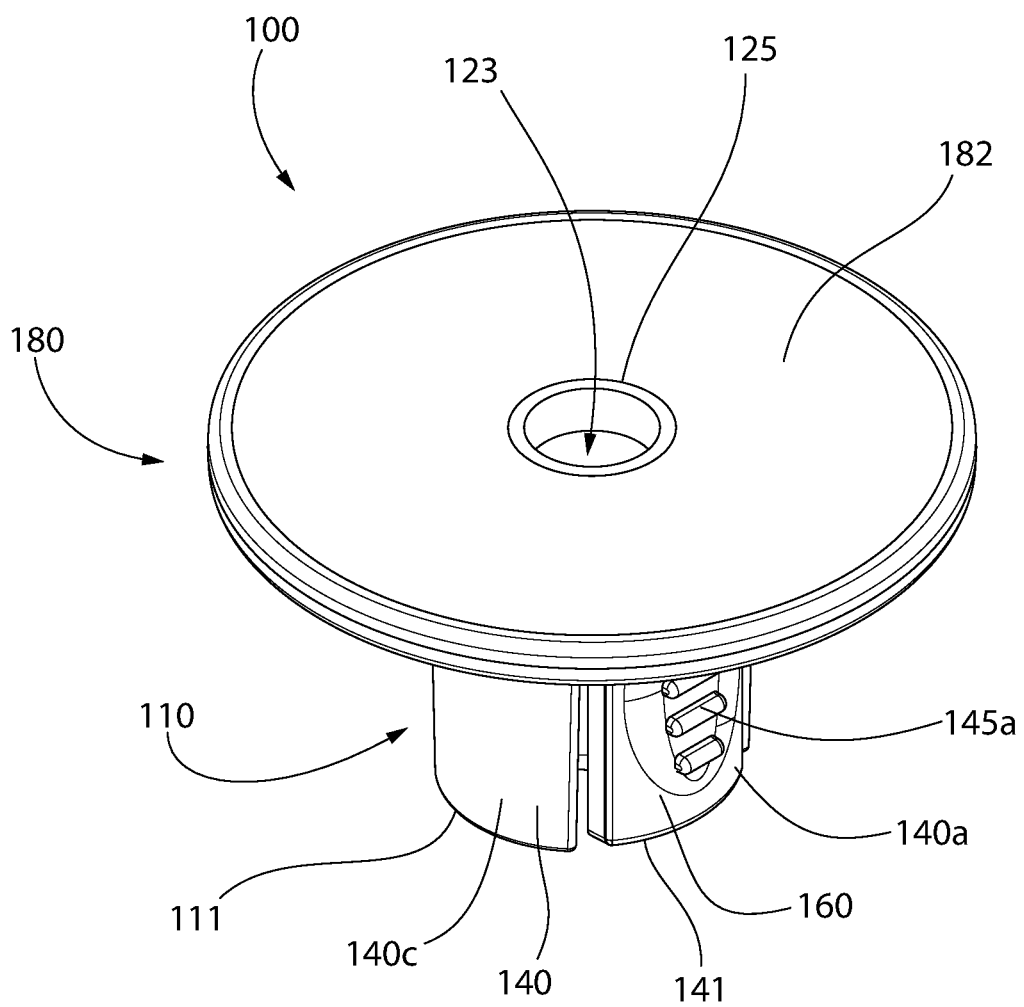
FIG. 1 is a top perspective view of an syringe capping and uncapping device in accordance with an embodiment of the present invention.
Figure 2:
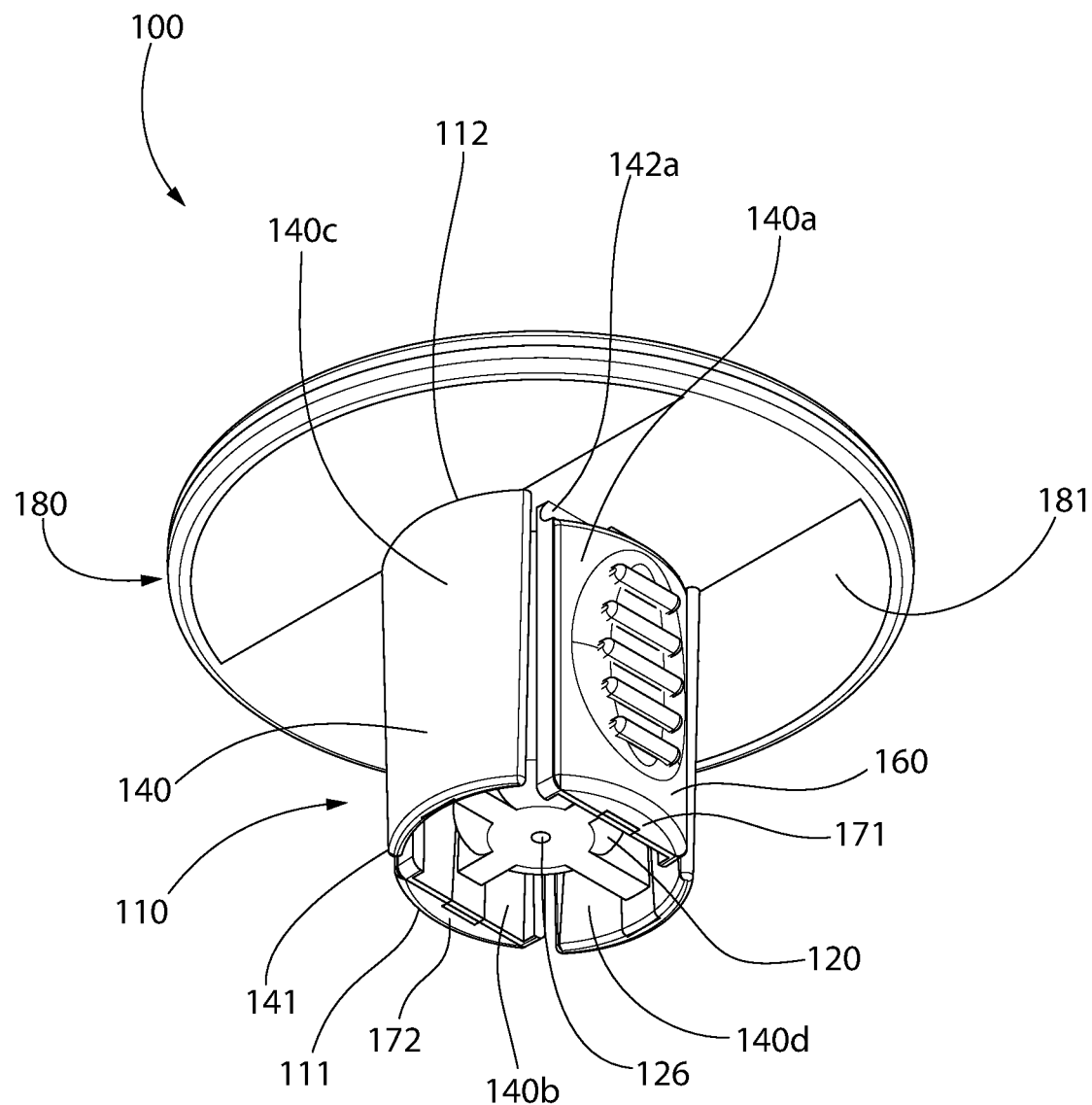
FIG. 2 is a bottom perspective view of the syringe capping and uncapping device of FIG. 1.
Figure 3:
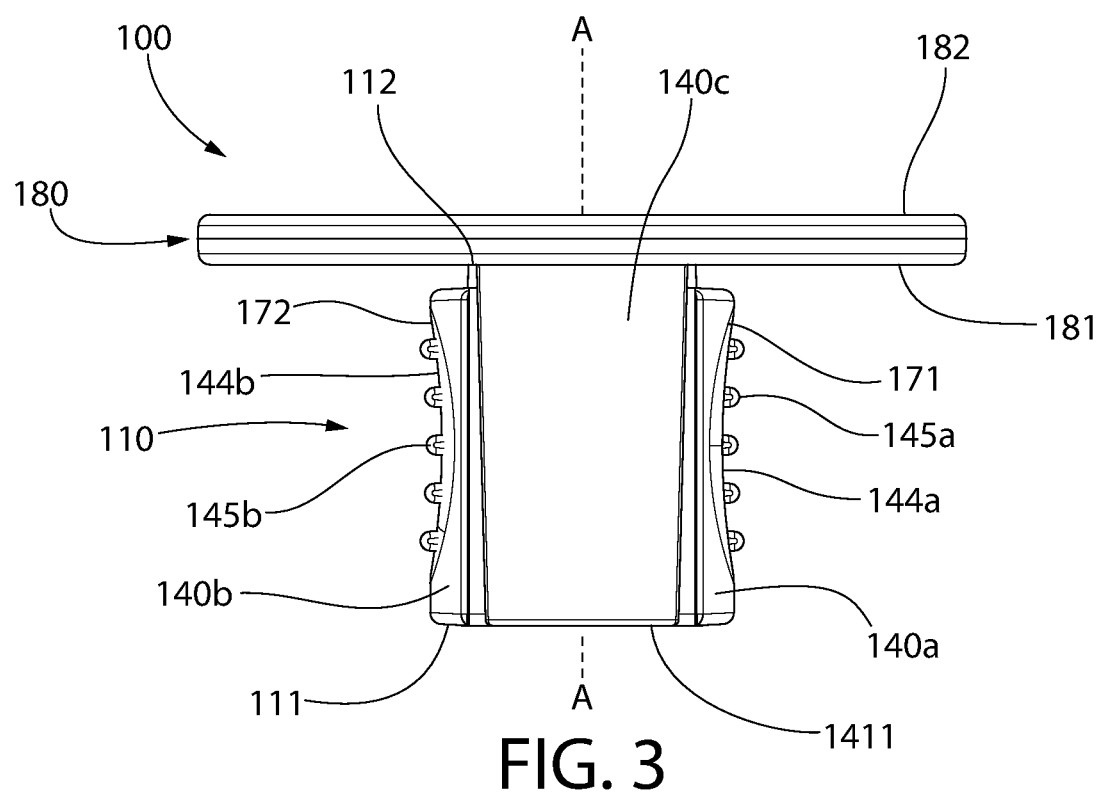
FIG. 3 is a front view of the syringe capping and uncapping device of FIG. 1.

The following description of the preferred embodiment(s) is merely exemplary in nature and is in no way intended to limit the invention, its application, or uses.

The description of illustrative embodiments according to principles of the present invention is intended to be read in connection with the accompanying drawings, which are to be considered part of the entire written description. In the description of the exemplary embodiments of the invention disclosed herein, any reference to direction or orientation is merely intended for convenience of description and is not intended in any way to limit the scope of the present invention. Relative terms such as "lower," "upper," "horizontal," "vertical," "above," "below," "up," "down," "left," "right," "top," "bottom," "front" and "rear" as well as derivatives thereof (e.g., "horizontally," "downwardly," "upwardly," etc.) should be construed to refer to the orientation as then described or as shown in the drawing under discussion. These relative terms are for convenience of description only and do not require that the apparatus be constructed or operated in a particular orientation unless explicitly indicated as such. Terms such as "attached," "affixed," "connected," "coupled," "interconnected," "secured" and similar refer to a relationship wherein structures are secured or attached to one another either directly or indirectly through intervening structures, as well as both movable or rigid attachments or relationships, unless expressly described otherwise. Moreover, the features and benefits of the invention are described by reference to the exemplary embodiments illustrated herein. Accordingly, the invention expressly should not be limited to such exemplary embodiments, even if indicated as being preferred. The discussion herein describes and illustrates some possible non-limiting combinations of features that may exist alone or in other combinations of features. The scope of the invention is defined by the claims appended hereto.

Referring first to FIGS. 1-7 concurrently, a syringe capping and uncapping device 100 (hereinafter "the device 100") will be described in accordance with an embodiment of the present invention. The device 100 serves several functions. First, the device 100 allows a user to easily detach a syringe needle from its cap or protective sheath without the user physically contacting the cap. Second, the device 100 allows a user to easily reattach the cap onto the syringe needle without the user having to physically hold the cap. And third, the device 100 is a guard that significantly reduces any chance that the syringe needle will pierce the user's skin during the capping or uncapping operations.

The device 100 generally comprises a body portion 110 and a flange portion 180. Both the body portion 110 and the flange portion 180 have features which will protect a user's hand from being pierced by the syringe needle during capping and uncapping operations. In particular, in the exemplified embodiment body portion 110 and the flange portion 180 are both formed from two materials, including a resilient material and a rigid material. The combination of these two materials offers significant protection to a user against accidental needle sticks, while also enabling the device 100 to maintain some flexibility to allow it to be used for uncapping operations. That is, the flexibility of the materials, particularly along the body portion 110, allows a user to uncap the syringe needle (i.e., remove the cap or protective sheath from the syringe needle) while the cap is located within the body portion 110 of the device 100. Thus, a user can insert the capped syringe needle into an interior of the body portion 110 such that the cap nests within the interior of the body portion 110. The user can remove the cap from the syringe needle while the cap remains located within the interior of the body portion 110. The user can then recap the syringe needle by inserting the syringe needle back into the cap which is positioned within the interior of the body portion 110 of the device 100. The flange portion 180 and the body portion 110 will protect the user's hand from being pricked or otherwise penetrated by the needle.

The body portion 110 of the device 100 extends from a bottom end 111 to a top end 112 along a longitudinal axis A-A. The body portion 110 comprises a receptacle 120, a guard wall 140, and an overlay structure 170. The receptacle 120 and the overlay structure 170 are integrally formed as a monolithic component. The guard wall 140 is not formed integrally with the receptacle 120 and the overlay 170 in the exemplified embodiment. In particular, in the exemplified embodiment the receptacle 120 and the overlay 170 are formed from a first material and the guard wall 140 is formed from a second material that is different than the first material. The first material is preferably a resilient material such as a thermoplastic elastomer. The second material is preferably a rigid material such as a hard plastic. Of course, the second material could take on other forms, such as being a metal or other hard or rigid material in other embodiments.

The receptacle 120 comprises an inner surface 121 and an outer surface 122. The inner surface 121 of the receptacle 120 defines a cavity 123 of the receptacle 120. The cavity 123 of the receptacle 120 extends from a floor 124 to an opening 125. The opening 125 is surrounded by the flange portion 180 of the device 100. Thus, the flange portion 180 is an annular flange 180 and the opening 125 is located at a center of the flange portion 180. The opening 125 forms a passageway into the cavity 123 of the receptacle 120 of the body portion 110 of the device 100. In the exemplified embodiment, the receptacle 120 has a generally cylindrical shape which somewhat corresponds to the shape of the cap of the syringes intended for use with the device 100. However, the invention is not to be so limited in all embodiments and the receptacle may have a non-circular shape in other embodiments. Furthermore, in the exemplified embodiment the cavity 123 is tapered such that the cross-sectional area of the cavity 123 of the receptacle 120 continuously decreases moving in an axial direction from the opening 125 to the floor 124. In other embodiments, the cavity 123 may be non-tapered and the cross-sectional area of the cavity 123 may be constant. As noted herein and discussed in greater detail below with reference to FIGS. 9A-12B, the cavity 123 is configured (i.e., sized and shaped) to receive and hold/retain a cap of a syringe.

In the exemplified embodiment, there is a vent opening 126 located in the floor 124 of the cavity 123. The vent opening 126 extends axially from the floor 124 of the cavity 123 to a bottom end of the receptacle 120. The vent opening 126 allows air to enter and exit the cavity 123 during capping and uncapping operations to prevent vacuum from occurring particularly when the user is removing the cap from the syringe using the device 100. As will be discussed below, the user applies a squeezing force onto the receptacle 120 during uncapping, so the vent opening 126 allows air to evacuate the cavity 123 during the squeezing and to re-enter the cavity 123 upon cessation of the squeezing force.

Figure 7:
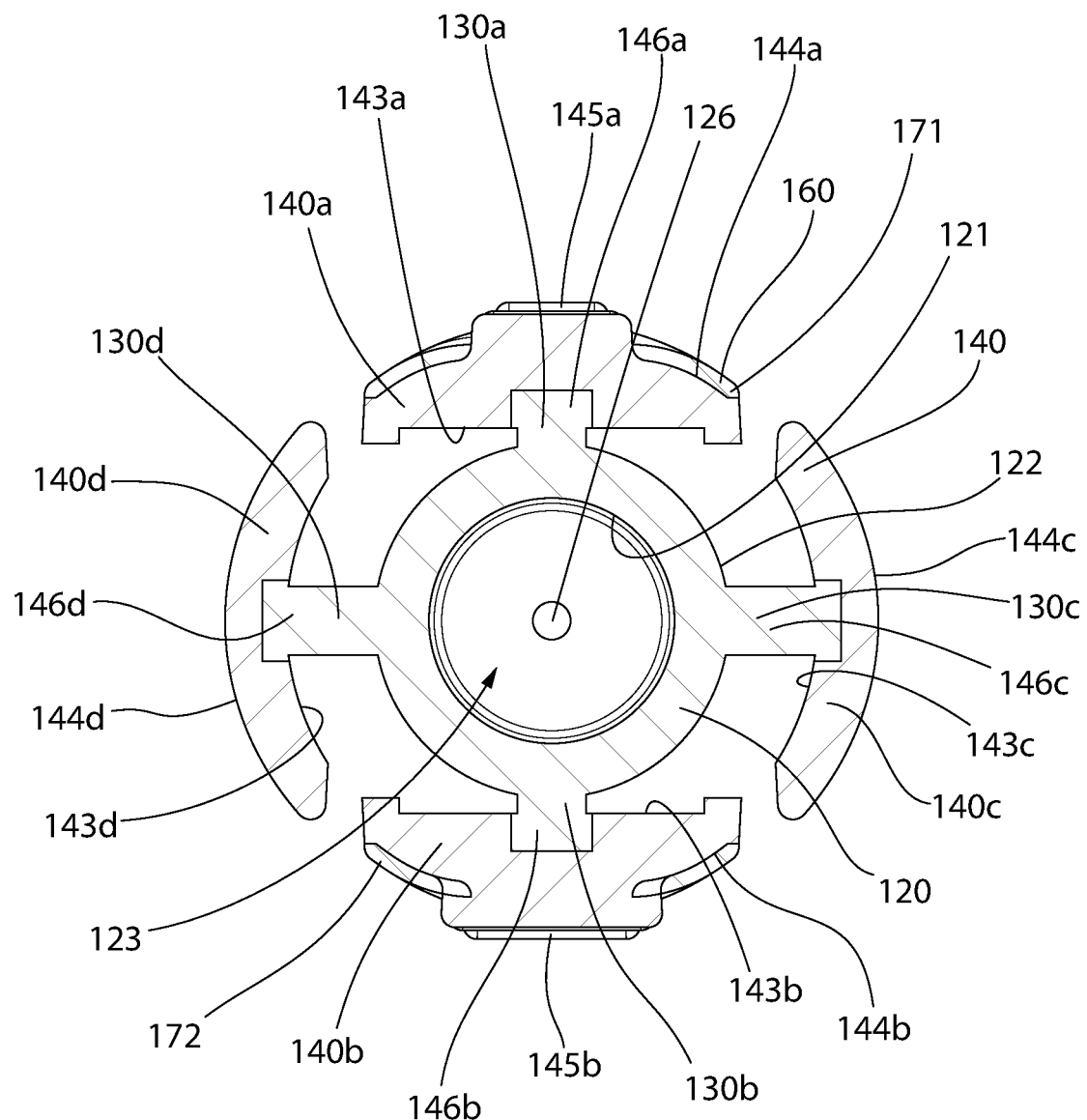
FIG. 7 is a cross-sectional view taken along line VII-VII of FIG. 5.

As noted above, the receptacle 120 is formed of a resilient material such as a thermoplastic elastomer in the exemplified embodiment. Thus, it is possible that the syringe needle could penetrate through the receptacle 120 if the syringe needle is inserted into the cavity 123 without the cap. Thus, in order to provide sufficient protection against needle sticks, the device 100 includes the guard wall 140 which surrounds the outer surface 122 of the receptacle 120. The guard wall 140 comprises a plurality of wall segments 140*a*, 140*b*, 140*c*, 140*d* that extend from a lower surface 181 of the flange portion 180 to a bottom end 141 of the guard wall 140. The plurality of wall segments 140*a-d* collectively circumferentially surround the receptacle 120. As best shown in FIG. 7, in the exemplified embodiment inner surfaces of the plurality of wall segments 140*a-d* are spaced apart from the outer surface 122 of the receptacle 120. However, this may not be required in all embodiments and one or more of the plurality of wall segments 140*a-d* may not be spaced from the outer surface 122 of the receptacle 120 in other embodiments.

Figure 4:
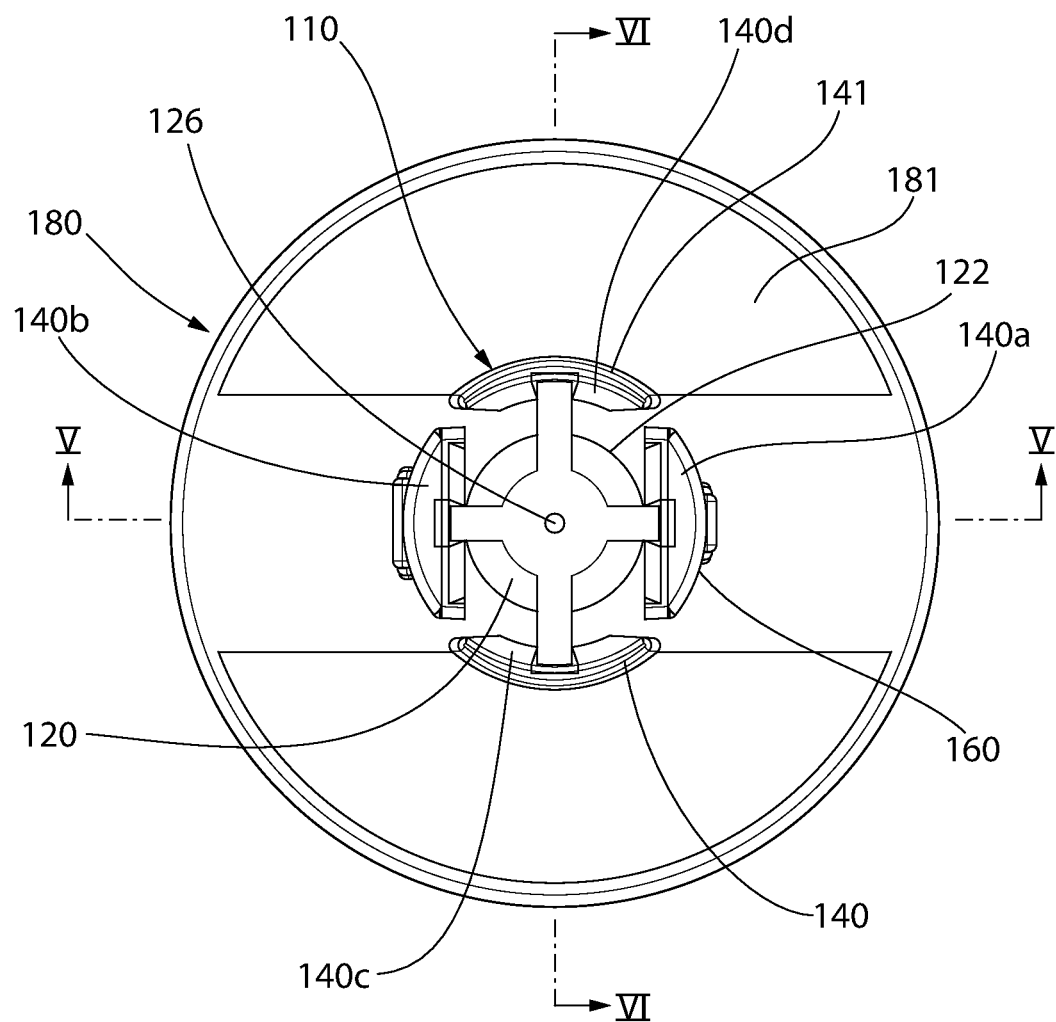
FIG. 4 is a bottom view of the syringe capping and uncapping device of FIG. 1.

The plurality of wall segments 140*a-d* are positioned in a circumferentially adjacent manner and in a circumferentially spaced apart manner. That is, each of the wall segments 140*a-d* is circumferentially adjacent to two of the other wall segments 140*a-d*, but each wall segment 140*a-d* is entirely spaced apart from each adjacent wall segment 140*a-d* moving in a circumferential direction. In particular, there is an axially elongated circumferential gap between each pair of adjacent ones of the wall segments 140*a-d* that extends the full length of the wall segments 140*a-d* from the lower surface 181 of the flange portion 180 to the bottom end 141 of the guard wall 140. As a result, in the exemplified embodiment the adjacent wall segments 140*a-d* are not at all attached to one another. This space or gap between the wall segments 140*a-d* is best illustrated in FIGS. 4 and 7, although it is also visible in FIGS. 1 and 2. Thus, each of the plurality of wall segments 140*a-d* is essentially a wall flap that extends from the lower surface 181 of the flange portion 180 to the bottom end 141 of the guard wall 140 independently of the other wall segments 140*a-d*. Each of the wall segments 140*a-d* may be able to flex inwardly and outwardly relative to the longitudinal axis A-A independently of the other ones of the wall segments 140*a-d*.

In the exemplified embodiment, the first and second wall segments 140*a*, *b* are pivotable wall segments whereas the third and fourth wall segments 140*c*, *d* are non-pivotable wall segments. Of course, the third and fourth wall segments 140*c*, *d* may have some flexibility, but they are not designed to pivot and are therefore referred to herein as non-pivotable wall segments. The first and second wall segments 140*a*, *b* are designed and structured intentionally to allow them to pivot about a pivot axis. The first and second wall segments 140*a*, *b* therefore form a pair of pivotable wall segments that are positioned opposite one another (i.e., the centerpoints of the first and second wall segments 140*a*, *b* are located 180° apart from one another). Stated another way, the first and second wall segments 140*a*, *b* are located on opposite sides of a plane on which the longitudinal axis A-A lies.

The first wall segment 140*a* is coupled to the flange portion 180 by a first living hinge 142*a*. The second wall segment 140*b* is coupled to the flange portion 180 by a second living hinge (not visible in the provided figures, but identical to the first living hinge 142*a*). The first and second living hinges 142*a* are thinner regions of material as compared to the first and second wall segments 140*a*, 140*b* and to the flange portion 180 which allows the first and second wall segments 140*a*, 140*b* to readily pivot relative to the flange portion 180 about the first and second living hinges 142*a*. Thus, upon a user applying a squeezing force onto the first and second wall segments 140*a*, 140*b*, the first and second wall segments 140*a*, 140*b* will pivot inwardly towards one another and towards the longitudinal axis A-A. During such pivoting of the first and second wall segments 140*a*, 140*b*, the first and second wall segments 140*a*, 140*b* will press inwardly against the receptacle 120 from two opposing directions, thereby causing the receptacle 120 to be compressed inwardly towards/into the cavity 123. This action may be used for uncapping a syringe by squeezing the cap of the syringe to hold the cap in the cavity 123 as the syringe body is detached from the cap, as discussed in more detail below with reference to FIGS. 9A-12B.

Although in the exemplified embodiment the first and second wall segments 140*a*, 140*b* are coupled to the flange portion 180 via living hinges 142*a*, the invention is not to be so limited in all embodiments. In one alternative embodiment, the first and second wall segments 140*a*, 140*b* may be formed as floating buttons during a first shot in an injection molding process. In such an embodiment, a second overmold shot during the injection molding process will mold a material (i.e., a resilient material such as a thermoplastic elastomer) between the first and second wall segments 140*a*, 140*b* and the flange portion 180. This portion of the material located between the first and second wall segments 140*a*, 140*b* and the flange portion 180 will form a hinge that attaches the first and second wall segments 140*a*, 140*b* to the flange portion 180. Thus, this is an alternative structural arrangement that will still allow the first and second wall segments 140*a*, 140*b* to pivot as described herein for purposes of applying pressure on a syringe cap during an uncapping operation. Other manufacturing techniques for forming the pivotable wall segments may also be used including other styles of hinges or other manners of attachment of the pivotable wall segments 140*a*, 140*b* to the flange portion 180. The first and second wall segments 140*a*, 140*b* function as buttons that can be depressed by a user to compress the receptacle 120 inwardly into contact with the syringe cap to hold the syringe cap in the cavity 123 of the receptacle as the syringe is pulled away from the syringe cap.

The third and fourth wall segments 140*c*, 140*d* are attached to the flange portion 180, but not by a living hinge. Thus, there is no reduction in thickness at the location at which the third and fourth wall segments 140*c*, 140*d* attach to the lower surface 181 of the flange portion 180. Moreover, as described herein, all of the wall segments 140*a-d* are formed from a rigid material such as a hard plastic. Thus, because the third and fourth wall segments 140*c*, 140*d* are not attached to the flange portion 180 with a living hinge, they will have significantly reduced flexibility as compared to the first and second wall segments 140*a*, 140*b*. In other embodiments, it may be possible to couple the third and fourth wall segments 140*c*, 140*d* to the flange portion 180 with a living hinge similar to the first and second wall segments 140*c*, 140*d* to enable all of the wall segments 140*a-d* to have the same degree of flexibility.

The wall segments 140*a-d* have inner surfaces 143*a-d* and outer surfaces 144*a-d*. The inner and outer surfaces 143*c*, *d*, 144*c*, *d* of the third and fourth wall segments 140*c*, 140*d* are smooth surfaces. The first and second wall segments 140*a*, 140*b* each comprise a plurality of rib structures 145*a*, 145*b* protruding from their respective outer surfaces 144*a*, 144*b*. The plurality of rib structures 145*a*, 145*b* are elongated in a direction transverse to the longitudinal axis A-A and are spaced apart in the axial direction. The rib structures 145*a*, 145*b* provide an enhanced grip structure for when the user is squeezing the first and second wall segments 140*a*, 140*b* during an uncapping procedure. The rib structures 145*a*, 145*b* terminate at distal ends that are aligned along a concave line that extends in the axial direction, thereby forming a sort of depression for a user's thumb and/or fingers to fit within during squeezing. Of course, the third and fourth wall segments 140*c, d* could also include rib structures in alternative embodiments, particularly in embodiments whereby those wall segments are also pivotable.

The outer surfaces 144*a-d* of the wall segments 140*a-d* are convex in the exemplified embodiment. Thus, the outer surfaces 144*a-d* of the wall segments 140*a-d* along with the gaps between the wall segments 140*a-d* collectively form a cylindrical shape in the exemplified embodiment. That is, the exterior surface of the guard wall 140 as a whole has a cylindrical shape. In other embodiments, the wall segments 140*a-d* and the spaces therebetween could form other shapes, such as polygonal shapes including square, rectangular, hexagonal, octagonal, or the like. Moreover, in the exemplified embodiment the inner surfaces 143*c, d* of the third and fourth wall segments 140*c, d* are concave. Thus, the third and fourth wall segments 140*c, d* are arcuate wall segments. In the exemplified embodiment, the inner surfaces 143*a, d* of the first and second wall segments 140*a, b* are generally planar, but may be concave/arcuate in other embodiments.

The body portion 110 of the device 100 further comprises a plurality of connection posts 130*a-d*. Each of the connection posts 130*a-d* extends from the outer surface of the receptacle 120 to the inner surface 143*a-d* of one of the wall segments 140*a-d*. More specifically, in the exemplified embodiment the connection posts 130*a-d* are formed integrally with the receptacle 120 out of the resilient material. Each of the wall segments 140*a-d* has a channel 146*a-d* formed into its inner surface 143*a-d*. The distal ends of the connection posts 130*a-d* located furthest from the receptacle 120 nest within the channels 146*a-d* in the inner surfaces 143*a-d* of the wall segments 140*a-d*. This facilitates a coupling between the guard wall 140 of the body portion 110 and the receptacle 120 of the body portion 110, which are formed from different materials as noted herein. The connection posts 130*a-d* are elongated along the length of the receptacle 120 in the exemplified embodiment.

In the exemplified embodiment, the first and second connection posts 130*a, b* which extend from the receptacle 120 to the first and second wall segments 140*a, b* have a shorter length (measured between the receptacle 120 and the wall segments 140*a, b*) than the third and fourth connection posts 130*c, d* which extend from the receptacle 120 to the third and fourth wall segments 140*a, b*. In the exemplified embodiment, this is because the first and second wall segments 140*a, b* are squeezed in order to compress the receptacle 120 during a syringe uncapping operation. Thus, maintaining the first and second wall segments 140*a, b* closer to the receptacle 120 better facilitates this functionality of the device 100.

Finally, the body portion 110 also comprises the overlay structure 170. As noted above, unlike the guard wall 140, the overlay structure 170 is formed integrally with the receptacle 120. Thus, as will be discussed in greater detail below with particular reference to FIG. 8, the receptacle 120, the connection posts 130*a-d*, and the overlay structure 170 are formed integrally as part of one monolithic structure, and the guard wall 140 is formed as part of another monolithic structure. In manufacturing the device 100, the two structures are not manufactured separately and later assembled, but rather they are manufactured together in a two or more shot injection molding process or a 3D printing process. However, the two structures are formed from different materials (one rigid and one resilient) in the exemplified embodiment, as described herein.

Figure 5:
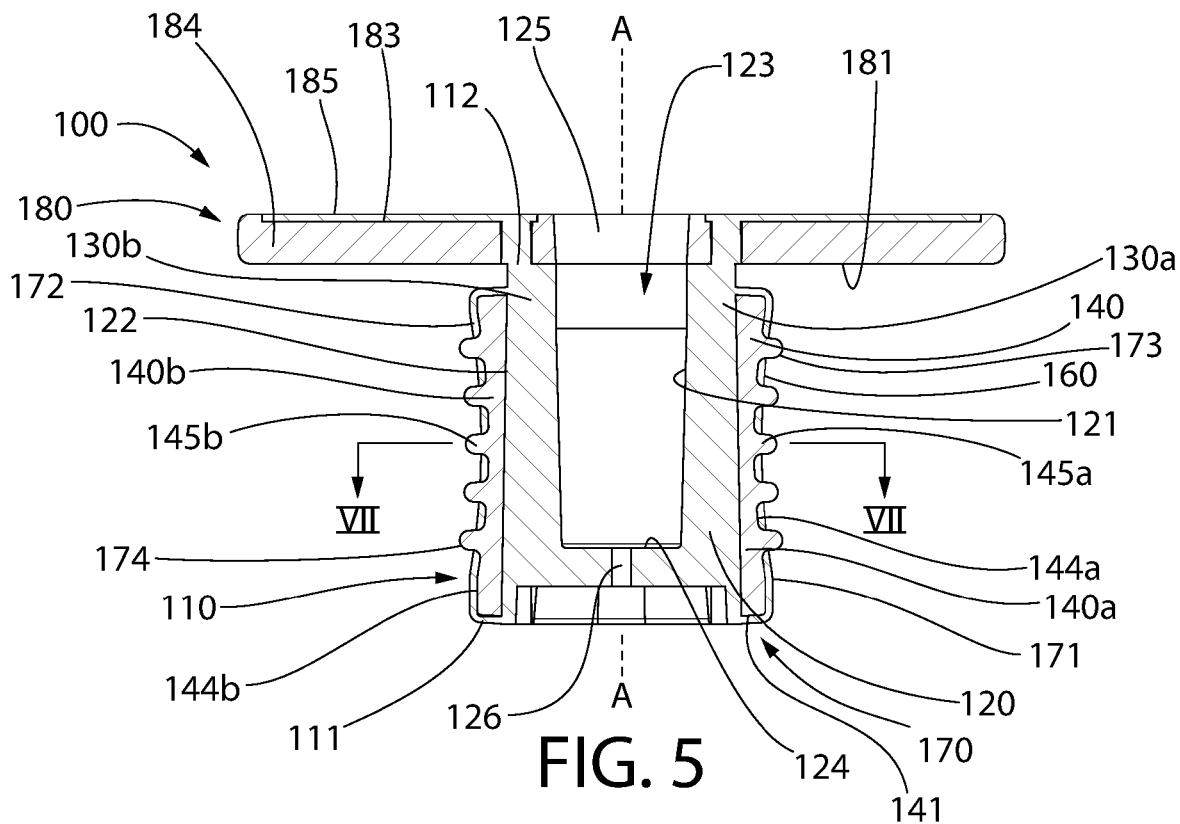
FIG. 5 is a cross-sectional view taken along line V-V of FIG. 4.

The overlay structure 170 comprises a first overlay wall 171 that is circumferentially and axially aligned with the first wall segment 140*a* of the guard wall 140 and a second overlay wall 172 that is circumferentially and axially aligned with the second wall segment 140*b* of the guard wall. While in the exemplified embodiment there are no overlay walls associated with or aligned with the third and fourth wall segments 140*c*, 140*d* of the guard wall 140, in alternative embodiments such additional overlay walls could be included. The first overlay wall 171 covers the outer surface 144*a* of the first wall segment 140*a* and the second overlay wall 172 covers the outer surface 144*b* of the second wall segment 140*b*. In fact, as best seen in FIG. 5, the first overlay wall 171 covers and is in direct surface contact with the outer surface 144*a* of the first wall segment 140*a* and the second overlay wall 172 covers and is in direct surface contact with the outer surface 144*b* of the second wall segment 140*b*. The first and second overlay walls 171, 172 are formed integrally with the receptacle 120 out of the resilient material. Covering the more rigid material of the first and second wall segments 140*a*, 140*b* with the resilient material of the first and second overlay walls 171, 172 enhances a user's grip on the wall segments that are configured to pivot. That said, the first and second overlay walls 171, 172 may be omitted in some embodiments without affecting the functionality of the device 100.

The first overlay wall 171 comprises a set of slots or openings 173 that are axially spaced apart. The second overlay wall 172 comprises a set of slots or openings 174 that are axially spaced apart. The slots or openings 173, 174 of the first and second overlay walls 171, 172 are aligned with the rib structures 145*a*, 145*b* of the first and second wall segments 140*a*, 140*b* of the guard wall 140. Thus, the rib structures 145*a* of the first wall segment 140*a* protrude through the openings 173 in the first overlay wall 171 and the rib structures 145*b* of the second wall segment 140*b* protrude through the openings 174 in the second overlay wall 172. In the exemplified embodiment, the outer surfaces of the first and second overlay walls 171, 172 are concave in the axial direction to form a depression within which a user's thumb and/or fingers may nest during uncapping procedures as described herein.

Having described the body portion 110 in some detail, the flange portion 180 will now be described. As mentioned above, the flange portion 180 is an annular flange in the exemplified embodiment which surrounds the opening 125 of the cavity 123. The flange portion 180 has the lower surface 181 and an upper surface 182, both of which are planar in the exemplified embodiment. In other embodiments, the upper and/or lower surfaces 181, 182 may not be planar, as this is not a required feature of the inventive device 100. The flange portion 180 forms a platform-like surface that significantly protects the user against accidental needle sticks. In particular, if a user misses the opening 125 when inserting the syringe needle into the cavity 123, the syringe needle will contact the flange portion 180, which will prevent the user from being pricked by the needle. The flange portion 180 is formed from both of the first (resilient) and second (rigid) materials, thereby providing an adequate barrier to protect the user.

In particular, the flange portion 180 comprises a first portion 183 that is formed integrally with the receptacle 120 (which may be described herein as a first portion of the body portion 110) and a second portion 184 that is formed integrally with the guard wall 140 (which may be described herein as a second portion of the body portion 110). The first portion 183 of the flange portion 180 comprises an upper section 185 and a lower section 186 that are spaced apart from one another. The upper and lower sections 185, 186 of the first portion 183 of the flange portion 180 are attached together by connection portions 188.

Figure 6:
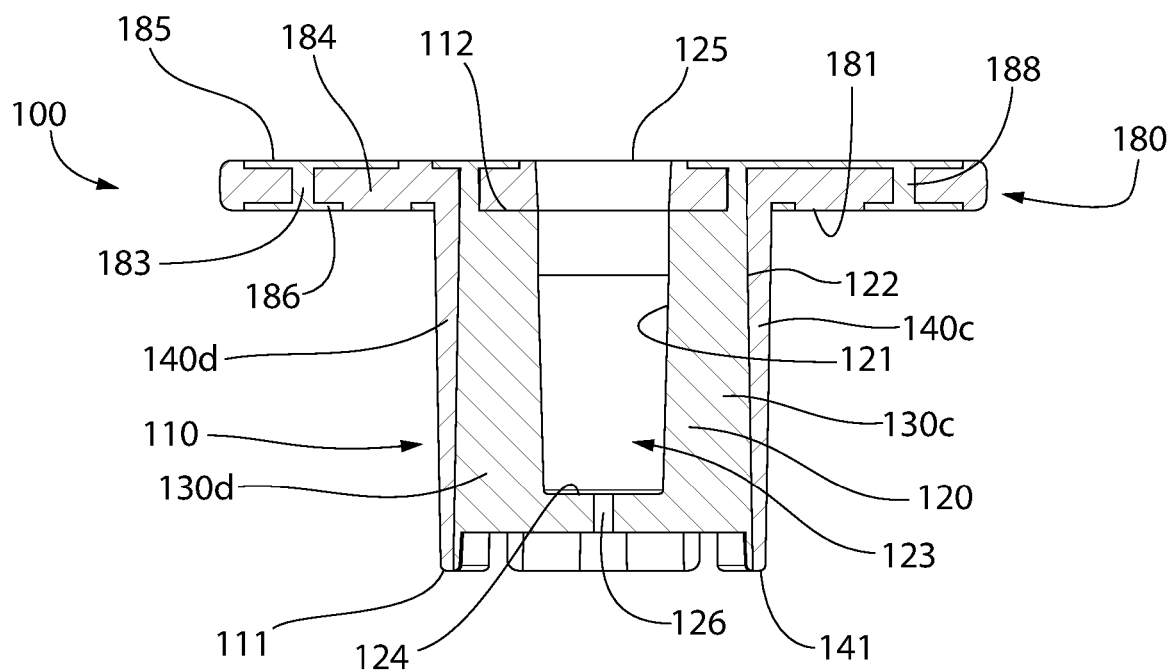
FIG. 6 is a cross-sectional view taken along line VI-VI of FIG. 4.

The second portion 184 of the flange portion 180 is disposed between the upper and lower sections 185, 186 of the first portion 183 of the flange portion 180. As seen in FIGS. 5 and 6, the upper section 185 of the first portion 183 of the flange portion 180 is flush with a top surface of the second portion 184 of the flange portion 180. Similarly, the lower section 186 of the first portion 183 of the flange portion 180 is flush with a bottom surface of the second portion 184 of the flange portion 180. The connection portions 188 of the first portion 183 of the flange 180 are disposed within ports that extend through the second portion 184 of the flange portion 180.

Figure 8:
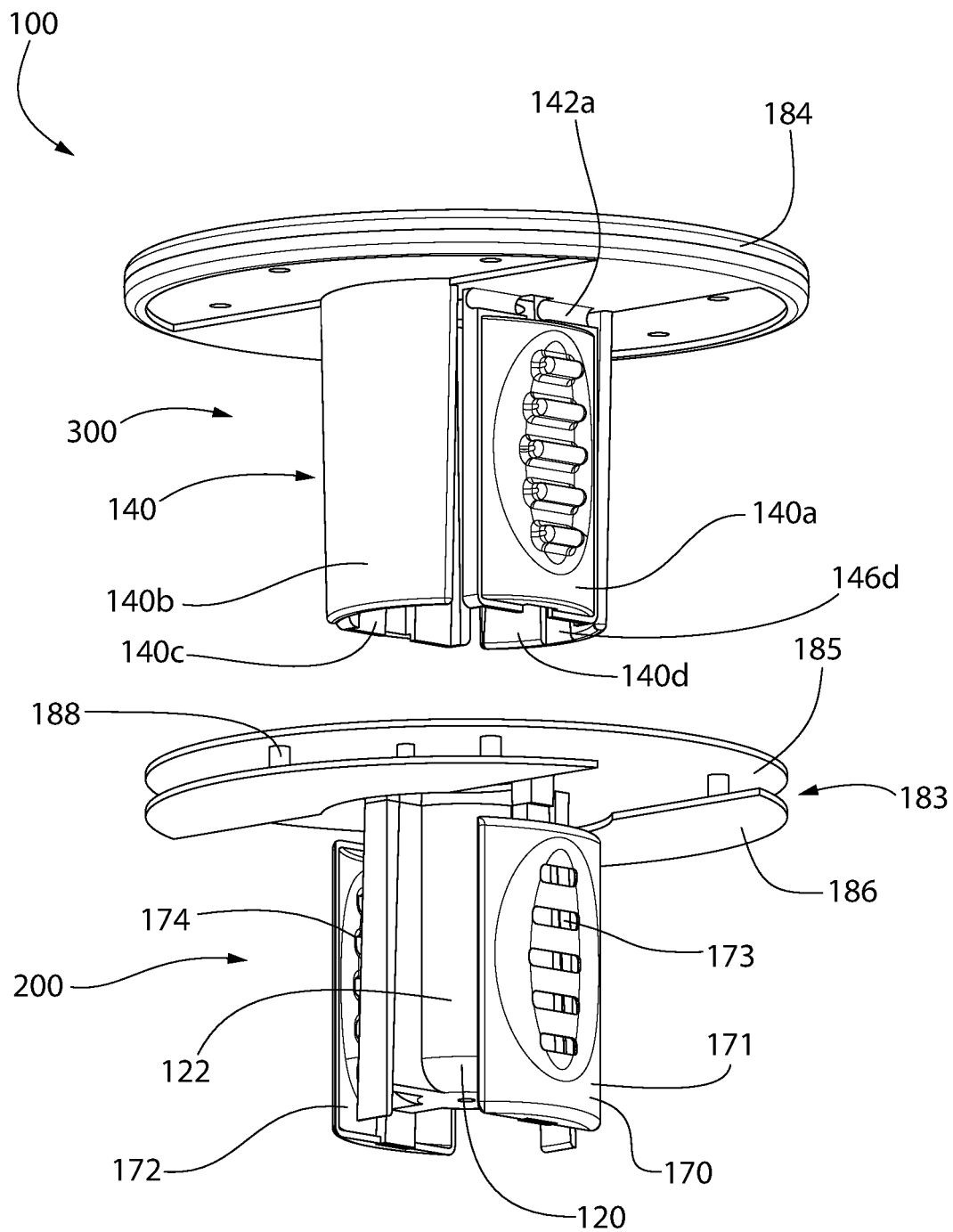
FIG. 8 is an exploded perspective view of the syringe capping and uncapping device of FIG. 1 illustrating first and second components thereof.

Referring to FIGS. 5, 6, and 8, the features which form parts of the separate components will be described. In particular, the device 100 comprises a first component 200 that is formed from the resilient material and a second component 300 that is formed from the rigid material. Thus, in some embodiments each of the first and second components 200, 300 may be formed as separate shots in an injection molding manufacturing process. In other embodiments, the device 100 may be formed by a 3D printing process out of multiple materials as described herein.

The first component 200 comprises the receptacle 120 of the body portion 110, the overlay structure 170 including the first and second overlay walls 171, 172, the connection posts 130a-d, and the upper and lower portions 185, 186 of the first portion 183 of the flange 180. The second component 300 comprises the guard wall 140 of the body portion 120 and the second portion 184 of the flange portion 180. As noted previously, the first and second wall segments 140a, 140b of the guard wall 140 are coupled to the second portion 184 of the flange portion 180 via the living hinges 142a. The third and fourth wall segments 140c, 140d are coupled to the second portion 184 of the flange portion 180, but not via a living hinge in the exemplified embodiment. When the first and second components 200, 300 are assembled together to form the device 100, the first and second wall segments 140a, 140b of the guard wall 140 are positioned between the first and second overlay walls 171, 172 and the receptacle 120.

Figure 9A:
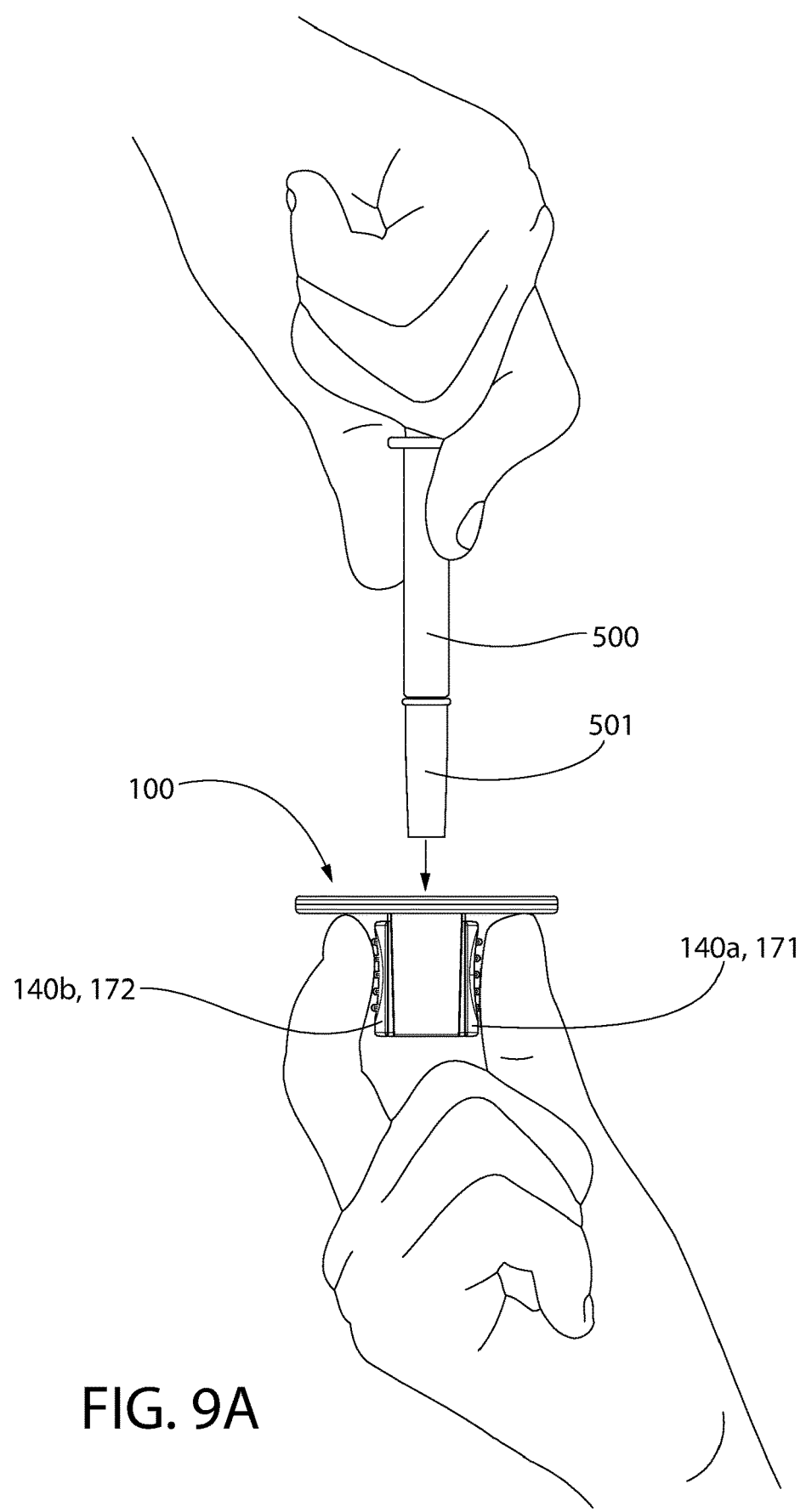
FIGS. 9A and 9B illustrate a user inserting a capped syringe into a cavity of the syringe capping and uncapping device of FIG. 1.
Figure 9B:
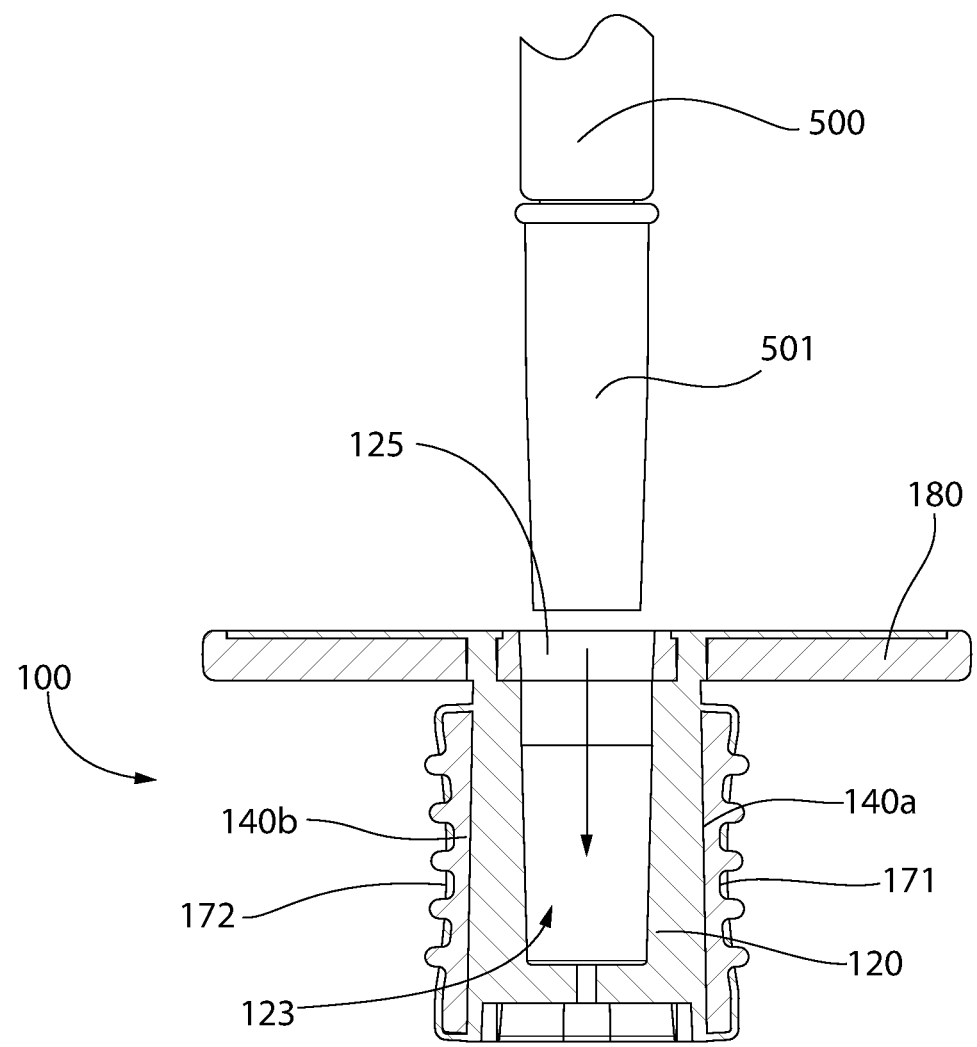

Referring to FIGS. 9A-12B sequentially, the use of the device 100 to remove a cap 501 from a syringe 500 and to reattach the cap 501 to the syringe 500 will be described. Referring first to FIGS. 9A and 9B, a user is holding a syringe 500 in one hand and the device 100 in the other hand with the cap 501 facing the device 100. In particular, the syringe 500 is positioned so that the cap 500 is aligned with the cavity 123 and its opening 125. The syringe 500 may be a staked syringe such that the cap 501 is removed with a simple pulling action. However, the device 100 may also work to cap and uncap luer lock syringes. In FIGS. 9A and 9B, the user has her thumb positioned on the first wall segment 140a (and its associated overlay wall 171) and one of her fingers positioned on the second wall segment 140b (and its associated overlay wall 172). However, during the insertion of the syringe 500 into the cavity 125 of the device 100, the specific placement of the user's fingers is not limiting of the invention. Specific placement of the user's fingers is only required during uncapping as described below.

Figure 10A:
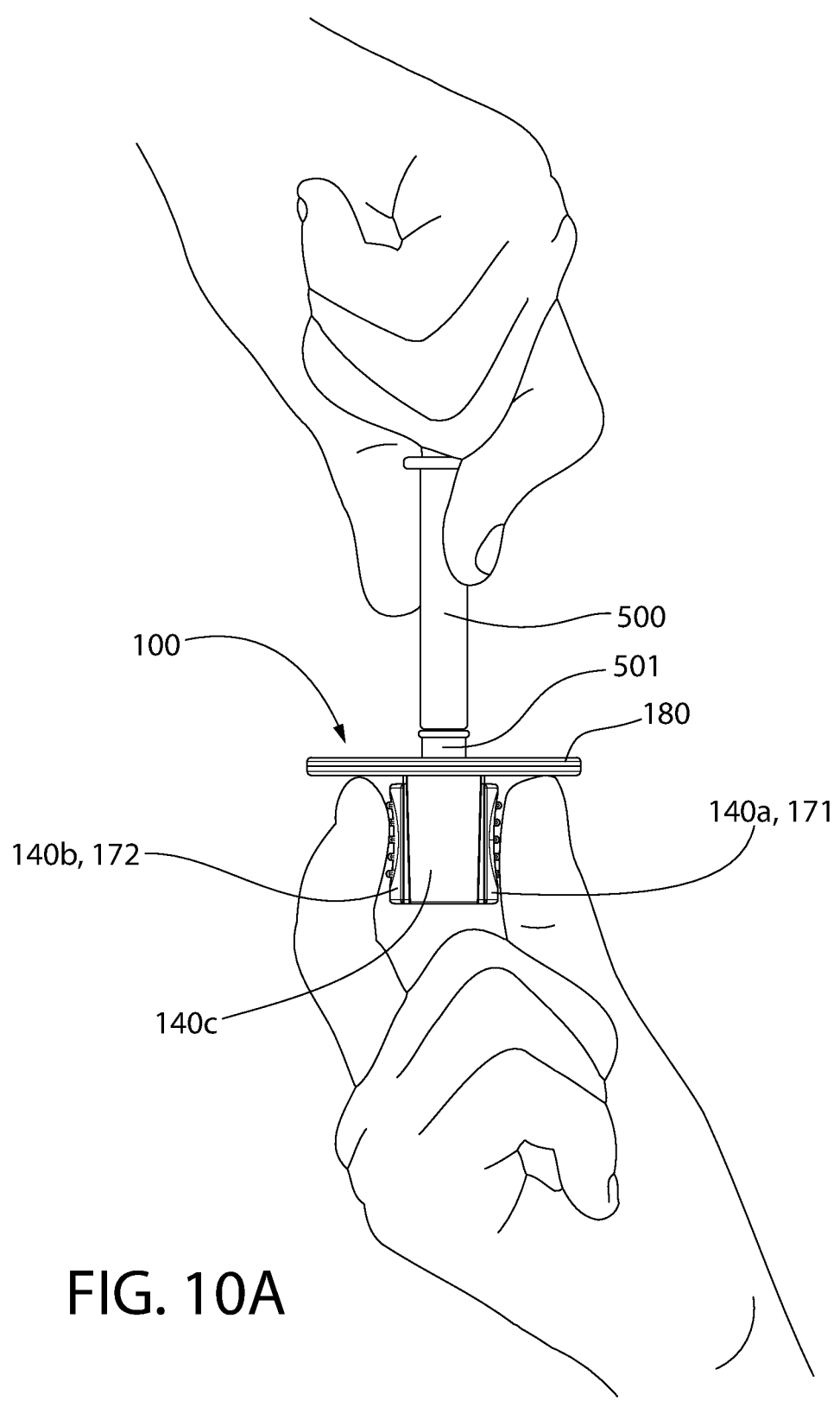
FIGS. 10A and 10B illustrate the capped syringe fully inserted into the cavity of the syringe capping and uncapping device of FIG. 1 while a user applies pressure onto opposing side walls thereof.
Figure 10B:
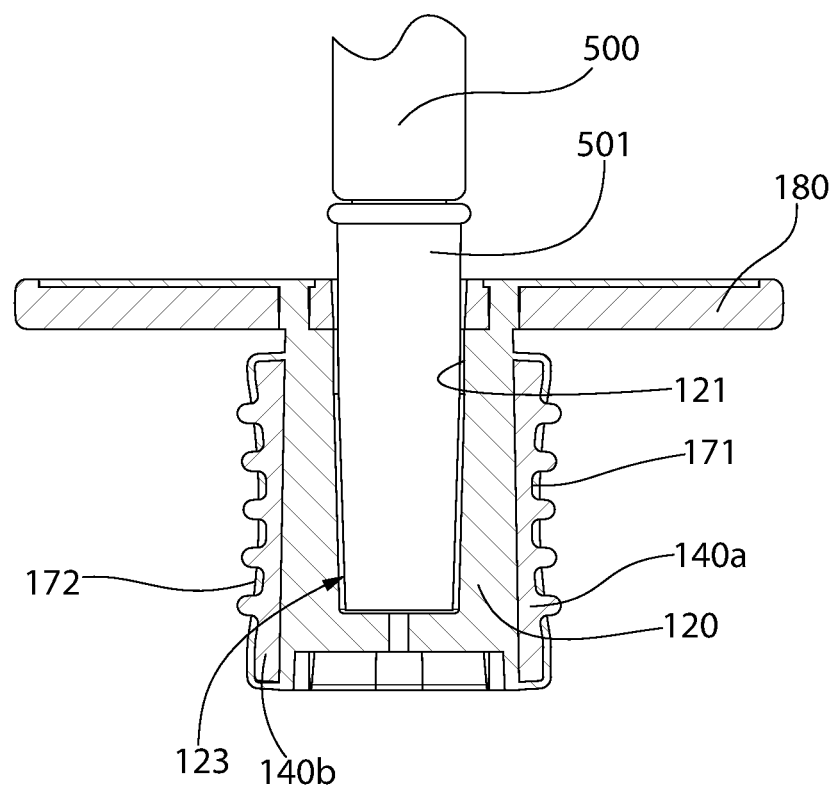

FIGS. 10A and 10B illustrate the device 100 with the cap 501 of the syringe 500 fully inserted into the cavity 123 of the device 100. In the exemplified embodiment, there is a slight gap between the inner surface 121 of the receptacle 120 and the outer surface of the cap 501, meaning the cross-sectional area of the cavity 123 is slightly larger than that of the cap 501. However, in other embodiments the fit between the cap 501 and the cavity 123 may be tighter or looser than that depicted. For example, the inner surface 121 of the receptacle 120 may be in physical contact with the outer surface of the cap 501 when the cap 501 is located in the cavity 123 even prior to a user squeezing the first and second wall segments 140a, 140b of the guard wall 140 as described herein.

Figure 11A:
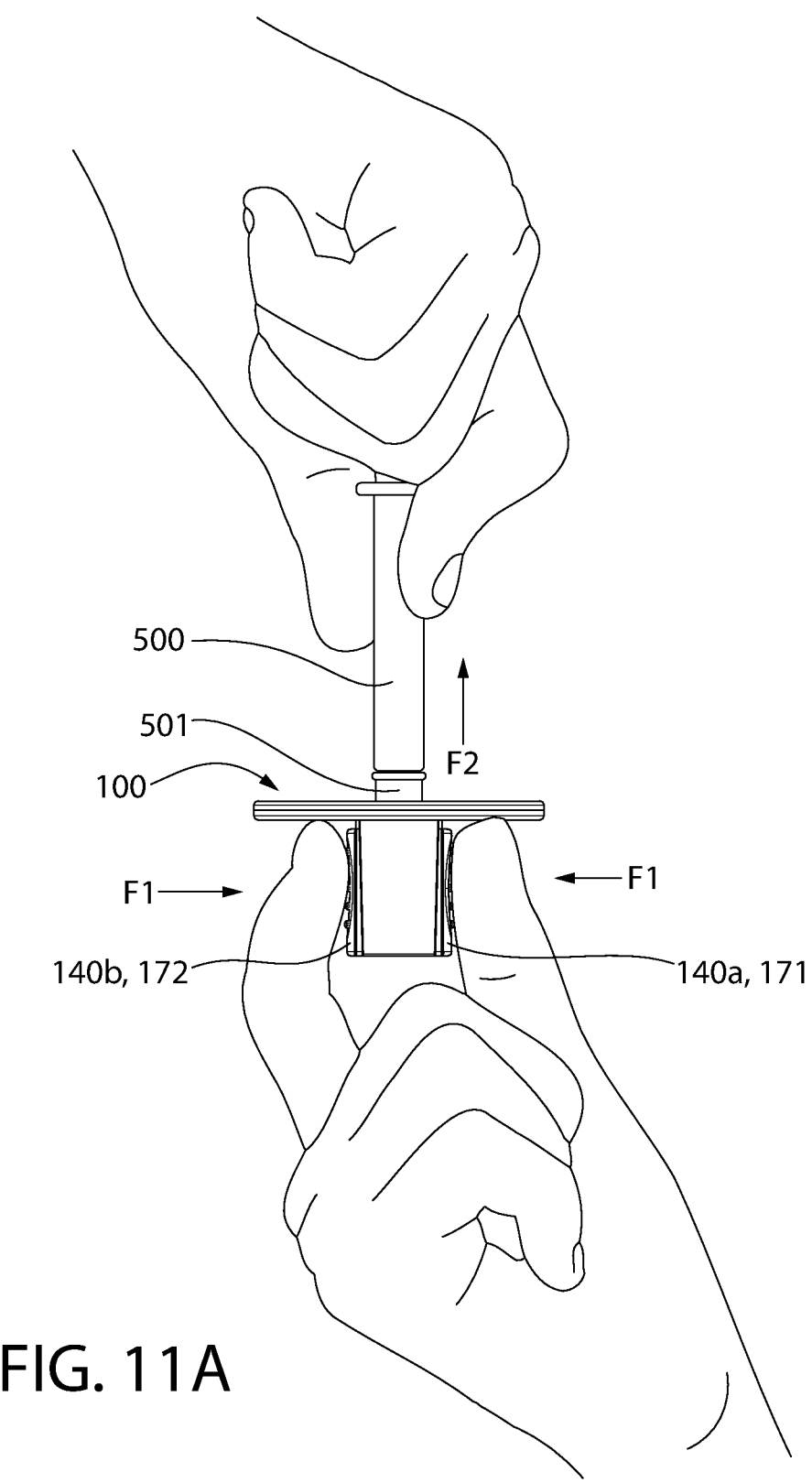
FIGS. 11A and 11B illustrate a user beginning to remove the syringe from the cavity of the syringe capping and uncapping device of FIG. 1 while the user applies pressure onto opposing side walls thereof to uncap the syringe.
Figure 11B:
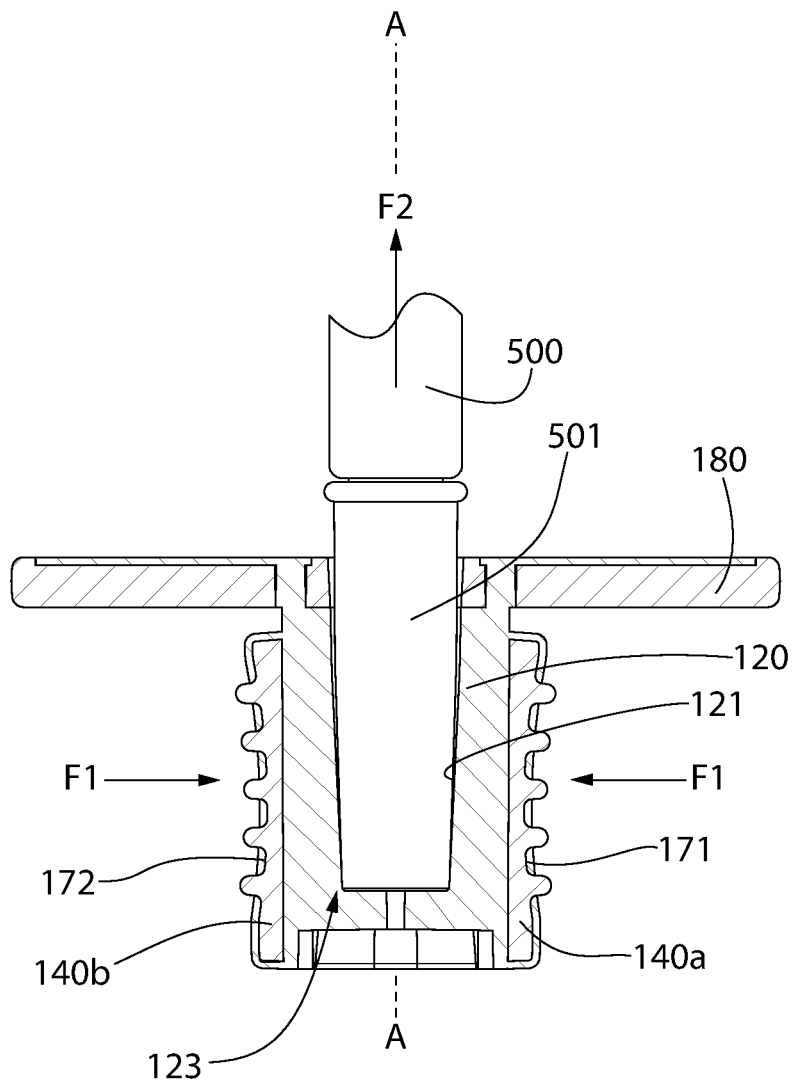

FIGS. 11A and 11B are identical to FIGS. 10A and 10B, except they include arrows to show the various forces that are being applied onto the device 100 and onto the syringe 500 by the user in order to separate the cap 501 from the syringe 500. Specifically, the cap 501 is still located within the cavity 123 of the receptacle 120. In order to uncap the syringe 500, the user applies opposing forces F1 onto the first and second wall segments 140a, 140b while simultaneously applying an axial pulling force F2 onto the syringe 500. The forces F1 being applied onto the first and second wall segments 140a, 140b causes the first and second wall segments 140a, 140b to pivot inwardly towards the longitudinal axis A-A about their respective living hinges (not visible in these figures). The pivoting of the first and second wall segments 140a, 140b causes the first and second wall segments 140a, 140b to apply pressure onto the receptacle 120, thereby causing the receptacle 120 to compress inwardly towards the longitudinal axis A-A and towards the cap 501 that is positioned within the cavity 123. Comparing FIGS. 10B and 11B, it can be seen that as a result of the forces F1 being applied onto the opposite wall segments 140a, 140b, the inner surface 121 of the receptacle 120 is now in contact with at least a portion of the cap 501. Thus, the user is applying a squeezing force onto the cap 501 through the device 100. At the same time as the squeezing force (the forces F1) is being applied onto the cap 501, the user is also pulling the syringe 500 in an axial direction away from the device 100 with the pulling force F2.

Figure 12A:
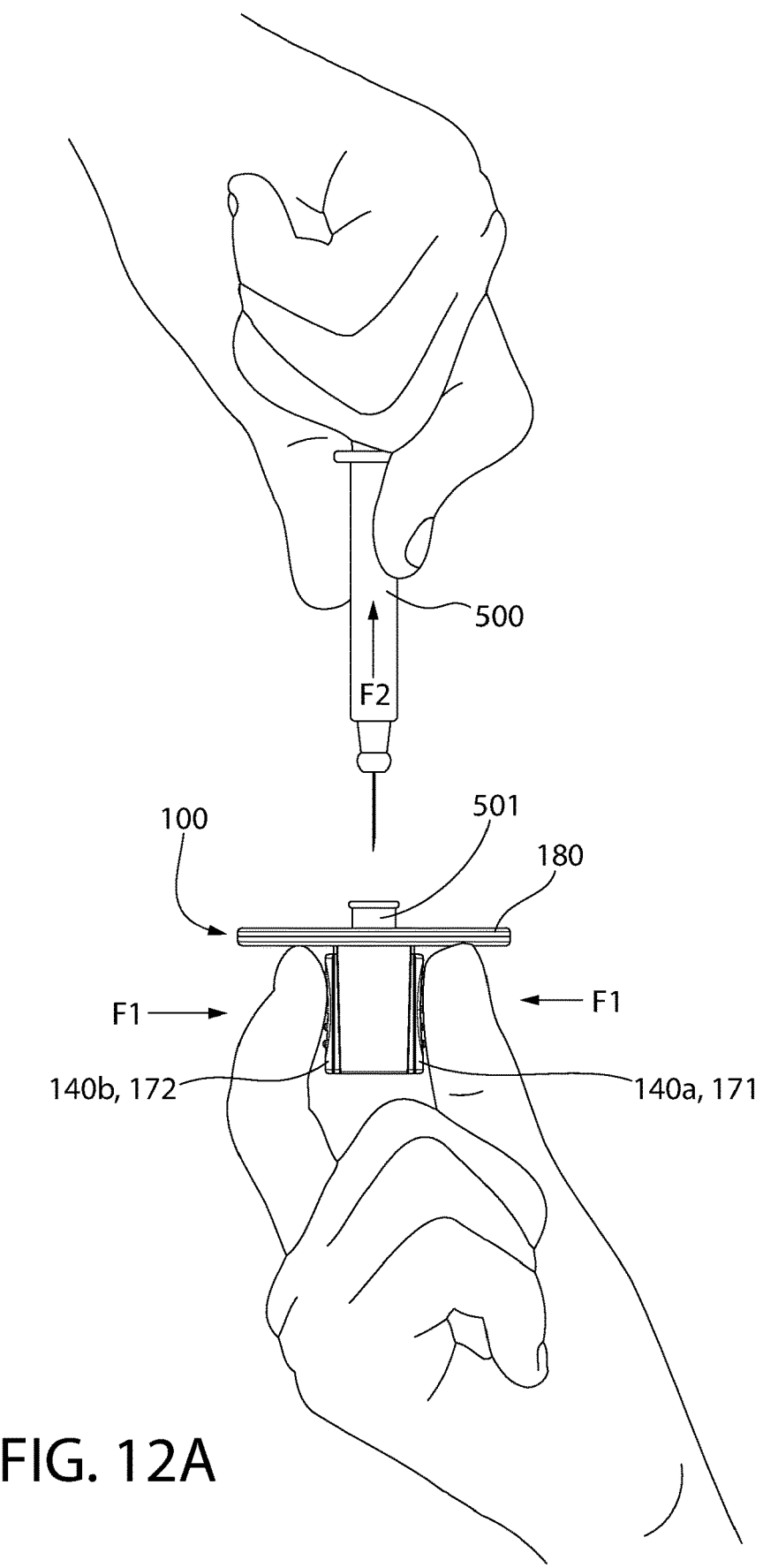
FIGS. 12A and 12B illustrate the uncapped syringe having been removed from the cavity of the syringe capping and uncapping device of FIG. 1 while the cap of the syringe remains located in the cavity of the syringe capping and uncapping device.
Figure 12B:
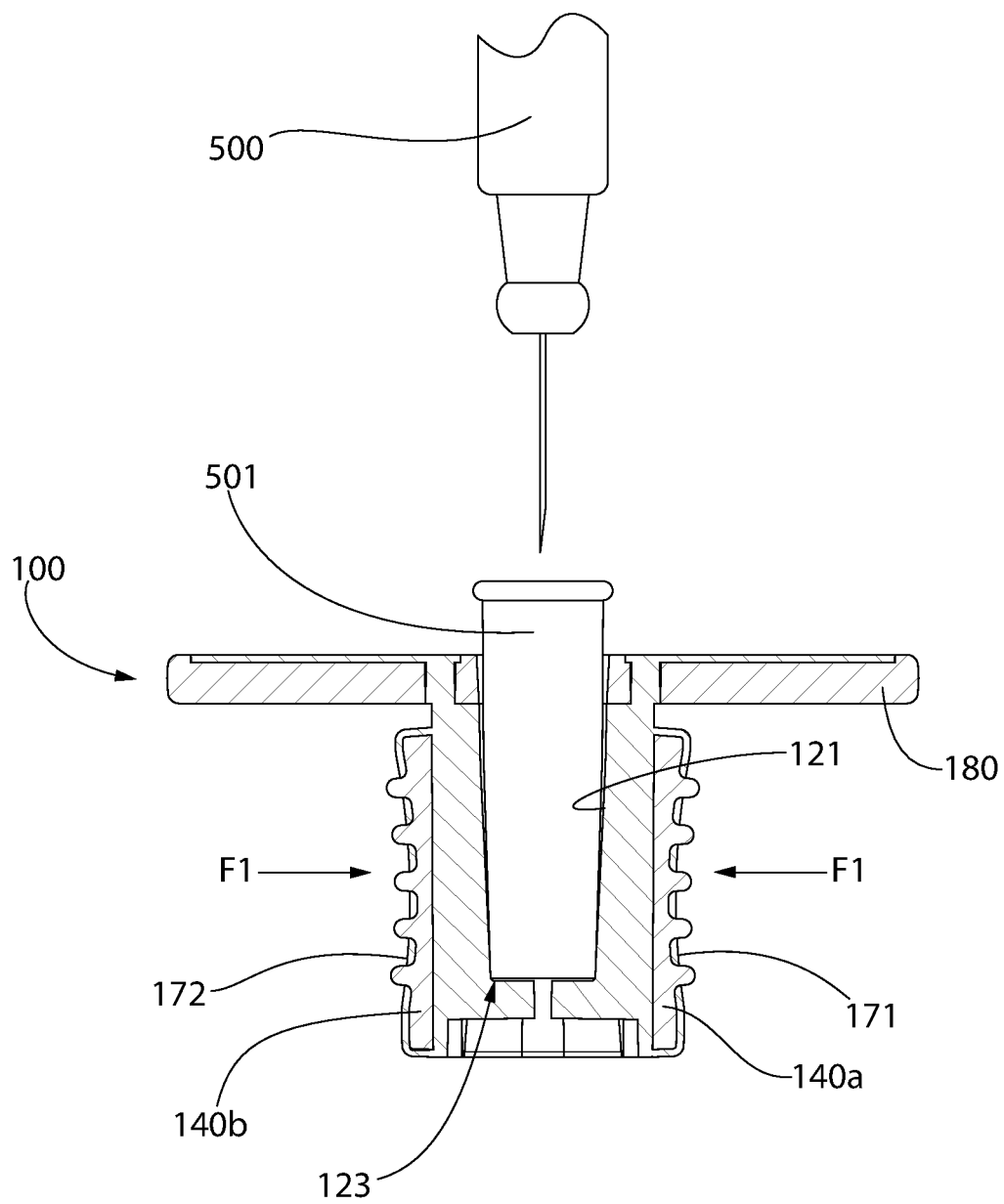

Referring to FIGS. 12A and 12B, as a result of the simultaneous squeezing forces F1 being applied onto the opposing first and second wall segments 140a, 140b and the axial pulling force F2 being applied onto the syringe 500, the syringe 500 is separated from the cap 501. In particular, the syringe 500 is pulled away from the cap 501 and the device 100 and the cap 501 remains nested within the cavity 123 of the receptacle 120 of the device 100. This occurs because the compression forces F1 applied onto the first and second wall segments 140a, 140b apply pressure on the cap 501 to hold the cap 501 within the cavity 123 even as the axial pulling force 500 is being applied onto the syringe 500. Thus, rather than the cap 501 being removed from the cavity 123 along with the syringe 500, the forces F1 serve to retain the cap 501 in the cavity 123 and allow for the syringe 500 to become detached or otherwise separated from the cap 501 and then removed from the cavity 123.

Furthermore, although not depicted, the device 100 can be used for recapping of the syringe 500 with the cap 501. Specifically, the user can insert the syringe 500 with the needle thereof facing downwardly back into the cap 501 while the cap 501 remains located within the cavity 123 of the device 100. The user need not apply any forces onto the guard wall 140 during the recapping procedure. Rather, the user simply inserts the needle of the syringe 500 back into the cap 501 until the cap 501 snaps into place on the syringe 500 indicating a positive attachment between the syringe 500 and the cap 501. Next, the user can simply pull the syringe 500 and cap 501 out of the cavity 123 by applying a pulling force onto the syringe 500 without also applying the squeezing force F2 onto the guard wall 140 of the device 100. During the recapping, the user's hand that is holding the device 100 is protected by the flange portion 180 and the body portion 110 of the device 100. The device 100 can also be used as a stand to simply hold the syringe 500 in an upright orientation. Specifically, the device 100 may be placed on a horizontal surface such as a desktop or the like while the syringe 500 is located within the cavity 123 to hold the syringe 500 in the upright orientation without it having to be held by a user.

While the invention has been described with respect to specific examples including presently preferred modes of carrying out the invention, those skilled in the art will appreciate that there are numerous variations and permutations of the above described systems and techniques. It is to be understood that other embodiments may be utilized and structural and functional modifications may be made without departing from the scope of the present invention. Thus, the spirit and scope of the invention should be construed broadly as set forth in the appended claims.

What is claimed is:

1. A syringe capping and uncapping device comprising:
   a flange portion having a lower surface and an upper surface;
   a body portion extending along a longitudinal axis, the body portion comprising:
      a receptacle extending from the lower surface of the flange portion, the receptacle having a cylindrical shape and comprising an inner surface that defines a cavity configured to receive and hold a cap of a syringe and an outer surface, the receptacle formed from a resilient material; and
      a guard wall extending from the lower surface of the flange portion and surrounding the outer surface of the receptacle, the guard wall comprising a plurality of wall segments, wherein adjacent ones of the plurality of wall segments are spaced apart by an axially elongated circumferential gap that extends from the lower surface of the flange portion to a bottom end of the guard wall, the guard wall formed from a rigid material;
   wherein the flange portion surrounds an opening that provides a passageway into the cavity of the receptacle of the body portion; and
   wherein upon applying a squeezing force onto opposing first and second wall segments of the plurality of wall segments, the first and second wall segments pivot inwardly relative to the flange portion towards the longitudinal axis and press against the receptacle from two opposing directions thereby causing the receptacle to be compressed inwardly towards the longitudinal axis to apply pressure onto the cap of the syringe that is positioned in the cavity while the syringe is pulled axially to remove the cap from the syringe.

2. The syringe capping and uncapping device according to claim 1 wherein the body portion comprises a plurality of connection posts, each of the plurality of connection posts extending from the outer surface of the receptacle to a different one of the plurality of wall segments.

3. The syringe capping and uncapping device according to claim 1 wherein the first and second wall segments are located on opposite sides of a plane on which the longitudinal axis lies, the first and second wall segments being attached to the flange portion by a living hinge such that applying the squeezing force onto the first and second wall segments in an inward direction towards the longitudinal axis causes the first and second wall segments to pivot inwardly about the living hinge to compress the receptacle.

4. The syringe capping and uncapping device according to claim 1 further comprising a first overlay wall aligned with and at least partially covering the first wall segments and a second overlay wall aligned with and at least partially covering the second wall segment, wherein the first and second overlay walls are formed integrally with the receptacle from the resilient material.

5. The syringe capping and uncapping device according to claim 4 wherein the first and second wall segments comprises a plurality of spaced apart ribs, and wherein each of the first and second overlay walls comprises a plurality of spaced apart openings such that the plurality of spaced apart ribs of the first wall segments protrude through the plurality of spaced openings of the first overlay wall and the plurality of spaced apart ribs of the second wall segments protrude through the plurality of spaced apart openings of the second overlay wall.

6. The syringe capping and uncapping device according to claim 5 wherein outer surfaces of the first and second overlay walls are concave in an axial direction, and wherein distal ends of the plurality of spaced apart ribs of each of the first and second wall segments are arranged along a concave line that extends in the axial direction.

7. The syringe capping and uncapping device according to claim 1 wherein the cavity comprises a floor, and further comprising a vent opening extending through the floor of the cavity.

8. The syringe capping and uncapping device according to claim 1 wherein the flange portion comprises a first portion formed integrally with the receptacle from the resilient material and a second portion formed integrally with the guard wall from the rigid material.

9. The syringe capping and uncapping device according to claim 1 wherein each of the plurality of walls has an inner surface that faces the outer surface of the receptacle, an entirety of the inner surfaces of each of the plurality of walls being spaced apart from the outer surface of the receptacle.

10. The syringe capping and uncapping device according to claim 9 further comprising a plurality of connection posts, each of the plurality of connection posts extending from the outer surface of the receptacle to the inner surface of one of the plurality of walls to couple the plurality of walls to the receptacle.

11. The syringe capping and uncapping device according to claim 1 wherein the resilient material is a thermoplastic elastomer and the rigid material is a hard plastic.

12. A syringe capping and uncapping device comprising:
   a body portion extending along a longitudinal axis, the body portion comprising:
      a receptacle comprising an outer surface and an inner surface defining a cavity configured to receive and hold a cap of a syringe;
      a guard wall circumferentially surrounding the outer surface of the receptacle, wherein the guard wall comprises a plurality of wall segments that are circumferentially spaced apart from one another; and a plurality of connection posts, each of the plurality of connection posts extending from the outer surface of the receptacle to a different one of the plurality of wall segments;

a flange portion extending radially outward from a top end of the body portion; and wherein at least a portion of the guard wall is pivotably coupled to the flange portion so that a force applied onto the portion of the guard wall in an inward direction towards the longitudinal axis causes the portion of the guard wall to pivot inwardly and compress the receptacle into forcible contact with the cap of the syringe to facilitate removal of the cap from the syringe.

13. The syringe capping and uncapping device according to claim 12 wherein the receptacle is formed from a resilient material and the guard wall is formed from a rigid material.

14. The syringe capping and uncapping device according to claim 12 wherein a first one of the plurality of wall segments and a second one of the plurality of wall segments that are positioned opposite one another are coupled to the flange portion by a living hinge so that the first and second ones of the plurality of wall segments form the at least a portion of the guard wall.

15. The syringe capping and uncapping device according to claim 14 further comprising an overlay structure formed integrally with the receptacle of the body portion, the overlay structure covering the first and second ones of the wall segments while leaving any remaining ones of the wall segments uncovered and exposed.

16. The syringe capping and uncapping device according claim 15 wherein the overlay structure comprises a first overlay wall that covers the first one of the plurality of wall segments and a second overlay wall that covers the second one of the plurality of wall segments, each of the first and second overlay walls comprising a plurality of spaced apart slots, and wherein the first and second ones of the wall segments each comprise a plurality of spaced apart rib structures that protrude through the slots in the first and second overlay walls.

17. The syringe capping and uncapping device according to claim 12 wherein the cavity of the receptacle is tapered such that a cross-sectional area of the cavity continuously decreases with increasing distance from the flange portion towards a floor of the cavity.

18. The syringe capping and uncapping device according to claim 12 wherein a first and a second one of the plurality of wall segments are pivotably coupled to the flange portion via a living hinge, and wherein the connection posts that are connected to the first and the second ones of the plurality of wall segments have a shorter length measured between the outer surface of the receptacle and inner surfaces of the first and second ones of the plurality of wall segments than any others of the connection posts.

19. A syringe capping and uncapping device comprising:
a body portion extending along a longitudinal axis, the body portion comprising:
 a receptacle comprising an outer surface and an inner surface defining a cavity configured to receive and hold a cap of a syringe; and
 a guard wall comprising a plurality of wall segments that are circumferentially adjacent to one another in a spaced apart manner to collectively surround the receptacle, the plurality of wall segments comprising a pair of pivotable wall segments;

a flange portion extending radially from a top end of the body portion, wherein the flange portion is formed integrally with the body portion; and wherein the pair of pivotable wall segments are pivotably coupled to the flange portion by a living hinge so that a force applied onto the pair of pivotable wall segments in an inward direction towards one another causes the pair of pivotable wall segments to pivot inwardly and compress the receptacle into forcible contact with the cap of the syringe to facilitate removal of the cap from the syringe.

20. The syringe capping and uncapping device according to claim 19 wherein the pair of wall segments comprise inner surfaces that face the outer surface of the receptacle, the inner surfaces of the pair of wall segments being spaced apart from the outer surface of the receptacle, and wherein a transverse axis that is perpendicular to the longitudinal axis intersects the guard wall and the receptacle.

* * * * *